(12) United States Patent
Keren et al.

(10) Patent No.: US 7,341,570 B2
(45) Date of Patent: Mar. 11, 2008

(54) APPARATUS AND METHODS FOR TREATING CONGESTIVE HEART DISEASE

(75) Inventors: Gadi Keren, Kiryiat Ono (IL); Ascher Shmulewitz, Mercer Island, WA (US)

(73) Assignee: Flowmedica, Inc., Fremont, CA (US)

( * ) Notice: Subject to any disclaimer, the term of this patent is extended or adjusted under 35 U.S.C. 154(b) by 754 days.

(21) Appl. No.: 10/613,654

(22) Filed: Jul. 3, 2003

(65) Prior Publication Data

US 2004/0097900 A1 May 20, 2004

Related U.S. Application Data

(63) Continuation of application No. 09/229,390, filed on Jan. 11, 1999, now Pat. No. 6,749,598.

(51) Int. Cl.
*A61M 25/00* (2006.01)
*A61M 29/00* (2006.01)

(52) U.S. Cl. ............ 604/96.01; 604/284; 606/194

(58) Field of Classification Search ........ 604/284, 604/523, 96.01–103, 93.01, 506–510; 606/108, 606/191, 194, 195
See application file for complete search history.

(56) References Cited

U.S. PATENT DOCUMENTS

| 1,696,018 A | 12/1928 | Schellberg |
| 2,499,045 A | 2/1950 | Walker et al. |
| 3,455,298 A | 7/1969 | Anstadt |
| 3,516,408 A | 6/1970 | Montanti |
| 3,667,069 A | 6/1972 | Blackshear et al. |
| 3,730,186 A | 5/1973 | Edmunds, Jr. et al. |
| 3,791,374 A | 2/1974 | Guarino |
| 3,841,331 A | 10/1974 | Wilder et al. |
| 3,995,623 A | 12/1976 | Blake et al. |
| 4,248,224 A | 2/1981 | Jones |
| 4,309,994 A | 1/1982 | Grunwald |
| 4,345,602 A | 8/1982 | Yoshimura et al. |

(Continued)

FOREIGN PATENT DOCUMENTS

DE 43 24 637 A1 3/1995

(Continued)

OTHER PUBLICATIONS

U.S. Appl. No. 09/165,333—Leschinsky, Boris—"Method and Apparatus for Treating Aneurysms".*

(Continued)

*Primary Examiner*—Matthew F. DeSanto
(74) *Attorney, Agent, or Firm*—Townsend and Townsend and Crew LLP

(57) ABSTRACT

Methods and apparatus are provided for treating congestive heart failure using a catheter having an inlet end configured for placement in the source of arterial blood such as the aorta, left ventricle or a femoral artery, and an outlet end having at least one conduit configured to be placed in the renal arteries. The catheter includes a lumen through which blood passes from the aorta or left ventricle directly to the renal artery, means for engaging the first conduit with renal artery. The means for engaging also may reduce backflow of blood into the abdominal aorta. The catheter preferably is configured to permit percutaneous, transluminal implantation. Methods of using and implanting the catheter are also provided.

32 Claims, 2 Drawing Sheets

U.S. PATENT DOCUMENTS

| | | | |
|---|---|---|---|
| 4,407,271 A | 10/1983 | Schiff | |
| 4,423,725 A | 1/1984 | Baran et al. | |
| 4,459,977 A | 7/1984 | Pizon et al. | |
| 4,490,374 A | 12/1984 | Bandurco et al. | |
| 4,493,697 A | 1/1985 | Krause et al. | |
| 4,536,893 A | 8/1985 | Parravicini | |
| 4,546,759 A | 10/1985 | Solar | |
| 4,554,284 A | 11/1985 | Stringer et al. | |
| 4,685,446 A | 8/1987 | Choy | |
| 4,705,502 A | 11/1987 | Patel | |
| 4,705,507 A | 11/1987 | Boyles | |
| 4,712,551 A | 12/1987 | Rayhanabad | |
| 4,714,460 A | 12/1987 | Calderon | |
| 4,723,939 A | 2/1988 | Anaise | |
| 4,753,221 A | 6/1988 | Kensey et al. | |
| 4,781,716 A | 11/1988 | Richelsoph | |
| 4,817,586 A | 4/1989 | Wampler | |
| 4,834,707 A | 5/1989 | Evans | |
| 4,846,831 A | 7/1989 | Skillin | |
| 4,861,330 A | 8/1989 | Voss | |
| 4,863,461 A | 9/1989 | Jarvik | |
| 4,888,011 A | 12/1989 | Kung et al. | |
| 4,902,272 A | 2/1990 | Milder et al. | |
| 4,902,291 A | 2/1990 | Kolff | |
| 4,906,229 A | 3/1990 | Wampler | |
| 4,909,252 A | 3/1990 | Goldberger | |
| 4,911,163 A | 3/1990 | Fina | |
| 4,919,647 A | 4/1990 | Nash | |
| 4,925,377 A | 5/1990 | Inacio et al. | |
| 4,925,443 A | 5/1990 | Heilman et al. | |
| 4,927,407 A | 5/1990 | Dorman | |
| 4,927,412 A | 5/1990 | Menasche | |
| 4,938,766 A | 7/1990 | Jarvik | |
| 4,950,226 A | 8/1990 | Barron | |
| 4,957,477 A | 9/1990 | Lundback | |
| 4,964,864 A | 10/1990 | Summers et al. | |
| 4,976,691 A | 12/1990 | Sahota | |
| 4,976,692 A | 12/1990 | Atad | |
| 4,990,139 A | 2/1991 | Jang | |
| 4,995,864 A | 2/1991 | Bartholomew et al. | |
| 5,002,531 A | 3/1991 | Bonzel | |
| 5,002,532 A | 3/1991 | Gaiser et al. | |
| 5,053,023 A | 10/1991 | Martin | |
| 5,059,178 A | 10/1991 | Ya | |
| 5,067,960 A | 11/1991 | Grandjean | |
| 5,069,680 A | 12/1991 | Grandjean | |
| 5,073,094 A | 12/1991 | Dorman et al. | |
| 5,089,019 A | 2/1992 | Grandjean | |
| 5,098,370 A | 3/1992 | Rahat et al. | |
| 5,098,442 A | 3/1992 | Grandjean | |
| 5,112,301 A | 5/1992 | Fenton et al. | |
| 5,112,349 A | 5/1992 | Summers et al. | |
| 5,119,804 A | 6/1992 | Anstadt | |
| 5,129,883 A | 7/1992 | Black | |
| 5,131,905 A | 7/1992 | Grooters | |
| 5,135,474 A | 8/1992 | Swan et al. | |
| 5,158,540 A | 10/1992 | Wijay et al. | |
| 5,163,910 A | 11/1992 | Schwartz et al. | |
| 5,167,628 A | 12/1992 | Boyles | |
| 5,180,364 A | 1/1993 | Ginsburg | |
| 5,205,810 A | 4/1993 | Guiraudon et al. | |
| 5,226,888 A | 7/1993 | Arney | |
| 5,256,141 A | 10/1993 | Gencheff et al. | |
| 5,257,974 A | 11/1993 | Cox | |
| 5,282,784 A | 2/1994 | Willard | |
| 5,290,227 A | 3/1994 | Pasque | |
| 5,308,319 A | 5/1994 | Ide et al. | |
| 5,308,320 A | 5/1994 | Safar et al. | |
| 5,312,343 A | 5/1994 | Krog et al. | |
| 5,320,604 A | 6/1994 | Walker et al. | |
| 5,326,374 A | 7/1994 | Ilbawi et al. | |
| 5,328,470 A | 7/1994 | Nabel et al. | |
| 5,332,403 A | 7/1994 | Kolff | |
| 5,345,927 A | 9/1994 | Bonutti | |
| 5,358,519 A | 10/1994 | Grandjean | |
| 5,364,337 A | 11/1994 | Guiraudon et al. | |
| 5,370,617 A | 12/1994 | Sahota | |
| 5,383,840 A | 1/1995 | Heilman et al. | |
| 5,397,307 A | 3/1995 | Goodin | |
| 5,421,826 A | 6/1995 | Crocker et al. | |
| 5,429,584 A | 7/1995 | Chiu | |
| 5,453,084 A | 9/1995 | Moses | |
| 5,464,449 A | 11/1995 | Ryan et al. | |
| 5,476,453 A | 12/1995 | Mehta | |
| 5,478,331 A | 12/1995 | Heflin et al. | |
| 5,484,385 A | 1/1996 | Rishton | |
| 5,505,701 A | 4/1996 | Anaya Fernandez de Lomana | |
| 5,509,428 A | 4/1996 | Dunlop | |
| 5,536,250 A | 7/1996 | Klein et al. | |
| 5,558,617 A | 9/1996 | Heilman et al. | |
| 5,599,306 A | 2/1997 | Klein et al. | |
| 5,609,628 A | 3/1997 | Keranen | |
| 5,613,949 A | 3/1997 | Miraki | |
| 5,613,980 A | 3/1997 | Chauhan | |
| 5,617,878 A | 4/1997 | Taheri | |
| 5,643,171 A | 7/1997 | Bradshaw et al. | |
| 5,643,215 A | 7/1997 | Fuhrman et al. | |
| 5,702,343 A | 12/1997 | Alferness | |
| 5,713,860 A | 2/1998 | Kaplan et al. | |
| 5,720,735 A | 2/1998 | Dorros | |
| 5,755,779 A | 5/1998 | Horiguchi | |
| 5,762,599 A | 6/1998 | Sohn | |
| 5,766,151 A | 6/1998 | Valley et al. | |
| 5,776,190 A | 7/1998 | Jarvik | |
| 5,797,876 A | 8/1998 | Spears et al. | |
| 5,807,895 A | 9/1998 | Stratton et al. | |
| 5,902,229 A | 5/1999 | Tsitlik et al. | |
| 5,902,336 A | 5/1999 | Mishkin | |
| 5,913,852 A | 6/1999 | Magram | |
| 5,928,132 A | 7/1999 | Leschinsky | |
| 5,935,924 A | 8/1999 | Bunting et al. | |
| 5,968,013 A | 10/1999 | Smith et al. | |
| 5,971,910 A | 10/1999 | Tsitlik et al. | |
| 5,984,955 A | 11/1999 | Wisselink | |
| 6,039,721 A | 3/2000 | Johnson et al. | |
| 6,068,629 A | 5/2000 | Haissaguerre et al. | |
| 6,077,256 A | 6/2000 | Mann | |
| 6,086,527 A | 7/2000 | Talpade | |
| 6,117,117 A | 9/2000 | Mauch | |
| 6,165,120 A | 12/2000 | Schweich et al. | |
| 6,287,608 B1 | 9/2001 | Levin et al. | |
| 6,387,037 B1 | 5/2002 | Bolling et al. | |
| 6,390,969 B1 | 5/2002 | Bolling et al. | |
| 6,468,241 B1 | 10/2002 | Gelfand et al. | |
| 6,482,211 B1 * | 11/2002 | Choi | 606/108 |
| 6,508,787 B2 | 1/2003 | Erbel et al. | |
| 6,733,474 B2 | 5/2004 | Kusleika | |
| 2001/0029349 A1 * | 10/2001 | Leschinsky | 604/101.03 |
| 2002/0169413 A1 | 11/2002 | Keren et al. | |
| 2004/0064089 A1 | 4/2004 | Kesten et al. | |

FOREIGN PATENT DOCUMENTS

| | | |
|---|---|---|
| EP | 0 654 283 A1 | 5/1995 |
| EP | 0 884 064 A2 | 12/1998 |
| GB | 2 239 675 A | 7/1991 |
| WO | WO 97/11737 | 4/1997 |
| WO | WO 98/03213 | 1/1998 |
| WO | WO 98/17347 | 4/1998 |
| WO | WO 98/52639 | 11/1998 |
| WO | WO 99/22784 | 5/1999 |
| WO | WO 99/33407 | 7/1999 |
| WO | WO 99/51286 | 10/1999 |
| WO | WO 00/41612 | 7/2000 |

| WO | WO 01/83016 | 4/2001 |
| WO | WO 01/41861 | 6/2001 |
| WO | WO 01/41861 A1 | 6/2001 |
| WO | WO 01/97687 | 12/2001 |
| WO | WO 01/97717 | 12/2001 |

OTHER PUBLICATIONS

Agostoni et al. Sustained Benefit from Ultrafiltration in Moderate Congestive heart failure Cardiology 2001:96 183-189.
Gruberg et al. The prognostic implications of further renal deterioration within 48 h of interventionary etc. J AM Coll Cardiol 2000, 20(5):540-548.
Halpenny et al. The effects of fendolopam on fenal blood flow and tubular function during aortic cross-clamping in anaesthetized dogs, EUR J Anatestheisol, Aug. 2000: 17(8); 491-8 Abstract.
Kini et al. A protocol for Prevention of Radiographic contrast Nepropathy etc. Catherization and Cardiovascular Interventions 2002, 55:169-173.
Kini et al. Managing the High-Risk Patient: Experience with Fenoldopam etc. Rev. Cardiovas Med 2001:2(suppl 1) S19-S25.
Madyoon, Use of Fenoldopam to Prevent Radiocontrast Nephropathy etc. Catherization and Cardiovascular Interventions 2001, 53:341-345.
Mathur et al., The effects of fenoldopam, a selective dopamine receptor agonist, on renal hemodynamics etc. Abstract only. Crit Cre Med Sep. 1999: 27(9) 1832-1837.
Muller et al. Prevention of Contrast Media Associated Nephropathy, Arch Intern Med, Feb. 2002, vol. 162 pp. 329-336.
Nohria et al. Medical Management of Advanced Heart Failure, JAMA, Feb. 6, 2002, vol. 162, pp. 628-640.
Tumlin et al. Fenoldopam mesylate blocks reductions in renal plasma flow after radiocontracts dye infusion, AM heart J 2002; 894-903.
Umrani et al., Beneficial effects of fenoldopam treatment on renal function in streptozotocin-induced diabetic rats, Clin Exp Hypertens, Apr. 24, 2002 (3): 207-19 Abstract only.
Zacherl et al. Periaterial Papverine Applications Improves Intraoperative Kidney Function etc. Journal of Surgical Research 103:268-271 (2002).
Margulies, et al., Intra-Arterial Atrial Natriuretic Factor (ANF) Attenuates Radiocontrast-Induced etc., Renal Pathology, unknown date, pp. 666, Abstract only.
Del Greco, The Kidney in Congestive Heart Failure, Modern Concepts of Cardiovascular Disease, Sep. 1975, vol. 44, No. 9, pp. 47-52.
Bischoff, W. et al.; "Modified in Situ Perfusion of the Kidney Using Balloon Catheters," vol. 94, No. 30, pp. 1695-1697, Oct. 21, 1976. Abstract Only.
Eisenberger, F. et al.; Transfemoral Cannulation of the Renal Vessels. Diagnostic and Therapeutic Use in Urology, Urologe [A], vol. 16, No. 1, pp. 1-5, Jan. 1977. Abstract Only.
Linden, R.J. et al.; "The Nature of the Atrial Receptors Responsible for a Reflex Decrease in Activity in Renal Nerves in the Dog," The Physiological Society, pp. 31-40, (1980).
Eisenberg, et al., Renal Failure After Major Angiography, Am J Med, Jan. 1980, vol. 68, pp. 43-46.
Eisenberg, et al., Renal Failure after Major Angiography Can Be Avoided with Hydration, AJR, May 1981; 136:859-861.
Thomas, et al. Influence of Bradykinin and Papaverine on Renal etc., Renal Physiology, Basel 5:197-205 (1982).
D'Elia, et al., Nephrotoxicity from angiographic Contrast Material, A prospective Study, Am J Med, May 1982, vol. 72, pp. 719-725.
Seiter, H. et al.; "Modified T-Catheter and Its Use for Transvenous Hypothermic in Situ Perfusion in the Surgical Restoration of the Kidney With Staghorn Calculi," Z. Urol Nephrol., vol. 76, No. 6, pp. 403-406, Jun. 1983. Abstract Only.
Thomas, et al. Glomerrular filtration dynamics renal vasodilation etc. Am. J. Physiol. 244:F606-F611 (1983).
Elkayam, et al., Renal Hemodynaic Effects of Vasodilation with Nifedipine and Hydralazine in Patients With Heart Failure, JACC Dec. 1984;vol. 4, No. 6, pp. 1261-1267.
Kehrer, G. et al.; "Construction and Experimental Application of a Catheter for Selective Arterial Kidney Perfusion in Situ," Urol. Res., vol. 13, No. 2, pp. 85-89,(1985). Abstract Only.
Mason, et al., Renal Dysfunction After Arteriography, JAMA, 1985;253:1001-1004.
Walker, H.S. et al.;Use of a Balloon-Tipped Perfusion Catheter for Renal Preservation During Suprarenal Abdominal Aortic Operations, J. Vasc. Surg., vol. 2, No. 2, pp. 337-339, Mar. 1985. Abstract Only.
Taliercio, et al., Risks for Renal Dysfunction with Cardiac Angiography, Annals of Internal Medicine, 1986;104:501-504.
Lass, et al., Cardiovascular and Renal Hemodynamic Effects of Intravenous Infusions of the Selective DA1 Agonist etc., Circulation 1988;78:1310-1315.
Vari et al., Induction , prevention and mechanisms of contrast media-induced acute renal failure, Kidney International, 1988; 33:669-707.
Parfrey, et al., Contrast Material-Induced Renal Failure in Patients with Diabetes Mellitus, Renal Insufficiency, or Both, N Engl J Med 1989; 320:143-149.
Schwab, et al., Contrast Nephrotoxicity: A Randomized Controlled Trial of a Nonionic and an Ionic Radiographic Contrast Agent, N Engl J Med, 1989, 320:149-153.
Margulies, et al., Induction and prevention of radiocontrast-induced nephropathy in dogs with heart failure, Kidney Int. 1990; vol. 38:1101-1108.
Akaba, N. et al.; "A Cylinder-Shaped Balloon Catheter for the Management of Dissecting Aneurysms in Acute Stage," Herz, vol. 17, No. 6, pp. 390-393, Dec. 1992. Abstract Only.
Kobayashi, A. et al.; "Experimental Study on the Usefulness of the Autoperfusion Balloon Catheter in Maintaining the Blood Supply to the Distal Organs," Nippon Igaku Hoshasen Gakkai Zasshi, vol. 52, No. 5, pp. 682-684, May.
Williams, D.M. et al.; "Design and Testing of a High-Flo2 Autoperfusion Catheter: An Experimental Study," J. Vasc. Interv. Radiol., vol. 3, No. 2, pp. 285-290, May 1992. Abstract Only.
Katsumata, T. et al.; "Newly-Developed Catheter for Cardio-Renmal Assist During Intraaortic Balloon Counterplusation," Kyobu Geka, vol. 46, No. 9, pp. 767-770, Aug. 1993. Abstract Only.
Patel, et al. Intravenous Fenoldopam Infusion in Severe Heart Failure, Cardiovasc Drugs Ther 1993;7:97-101.
Shusterman, et al. Fenoldopam, But Not Nitroprusside, Improves Renal Function etc. Am J of Medicine, 95:161-168 (1993).
Novick, A.C.; "Atherosclerotic Ischemic Nephropathy. Epidemiology and Clinical Considerations," Urol. Clin. North Am, vol. 21, No. 2, pp. 195-200, May, 1994. Abstract Only.
Solomon, et al., Effects of Saline, Mannitol, and Furosemide on Accute Decreases in Renal Function etc., N Engl J Med 1994; vol. 331 No. 21 pp. 1416-1420.
Strick, et al., Direct measurement of renal medullary blood flow in the dog, Am J. Physiol. 267 (Regulatory Integrative Comp. Physiol. 36): R253-R2259, 1994.
Levin, Howard R. et al.; "Reversal of Chronic Ventricular Dilation in Patients With End-Stage Cardiomyopathy by Prolonged Mechanical Unloading," vol. 91, No. 11, pp. 2717-2718, Jun. 1, 1995.
Masaki, Z. et al.:"In-Situ Perfusion by Retrograde Cannullation of a Tumor Artery for Nephron-Sparing Surgery," Int. J. Urol, vol. 2, No. 3, pp. 161-165, Jul. 1995. Abstract Only.
Rudnick, et al., Nephrotoxicity of ionic and noionic contrast media in 1196 patients: A randomized trial, Kidney International, 1995;47:254-261.
Cohn, Jay N.; "The Management of Chronic Heart Failure," The New England Journal of Medicine, pp. 490-498, Aug. 15, 1996.
Elkayam, et al., Renal Vasodilatory Effect of Endothelial Stimulation in Patients with Chronic Congestive Heart Failure, J Am Coll Cardiol 1996;28:176-182.
Iannone, L.A. et al—"Effect of Primary Balloon Expandable Renal Artery Stents on Long-Term Patency Renal Function and Blood Pressure in Hypertensive and Renal Insufficient Patients With Renal Artery Stenosis," Cathet. Cardiovase.

Greco, B.A. et al.; "Atherosclerotic Ischemic Renal Disease," Am J. Kidney Dis., vol. 29, No. 2, pp. 167-187, Feb. 1997. Abstract Only.

McCarthy, Animal Models in Medical Device Development and Qualification, Charles River laboratories, vol. 10(2) 1997.

McCullough, et al., Acute Renal Failure after Coronary Intervention: Incencence, Risk Factors, and Relationship to Mortality, Am J Med. 1997;103:368-375.

White, C.J. et al.; "Renal Artery Stent Placement: Utility in Lesions Difficult to Treat With Balloon Angioplasty," J. Am. Coll. Cardiol., vol. 30, No. 6, pp. 1445-1450, Nov. 15, 1997. Abstract Only.

Canaud, B. et al.; "Temporary Vascular Access for Extracorporeal Renal Replacement Therapies in Acute Renal Failure Patients," Kidney Int. Suppl., vol. 66, pp. S142-S150, May 1998. Abstract Only.

Drescher, et al., Prevention of Contrast Medium-Induced Renal Vasospasm by Phosphodiesterase Inhibition, Invest Radiol 1998;33:858-862.

Garwood, Susan et al.; "Renal Preservation Strategies for High Risk Patients," University of Chico School of Medicine, Cover Page, Table of Contents Page, pp. 1-19, (1998).

Jacobs, M.J. et al.; "Reduced Renal Failure Following Thoracoabdominal Aortic Aneurysm Repair by Selective Perfusion," Eur. J. Cardiothorac. Surg., vol. 14, No. 2, pp. 201-205, Aug. 1998. Abstract Only.

Mathis, J.M. et al.; "Use of a Guide Catheter as a Temporary Stent During Microcatheter Intervention," AJNR Am. J. Neuroradiol, vol. 19, No. 5, pp. 932-933, May 1998. Abstract Only.

Middleton, J.P.; "Iscremic Disease of the Kidney: How and Why to Consider Revascularization," J. Nephrol., vol. 11, No. 3, pp. 123-136, May-Jun. 1998. Abstract Only.

Postma, C.T. et al.; "Treatment of Renal Artery Stenosis With Intra-Arterial Stents," Ned Tijdschr Geneeskd, vol. 142, No. 39, pp. 2132-2137, Sep. 26, 1998. Abstract Only.

Bakris, et al., Renal hemodynamics in radiocontrast medium-induced renal dysfunction etc. Kidney International, vol. 56 pp. 206-210 (1999).

Bergey, E.A. et al.; "Transhepatic Insertion of Vascular Dialysis Catheters in Children: A Safe, Life-Prolonging Procedure," Pediatr. Radiol., vol. 29, No. 1, pp. 42-50, Jan. 1999. Abstract Only.

Fox, S. I.; "Mechanisms of Contraction," Human Physiology, Fourth Edition, pp. 300-323.

Heyman, et al., Pathophysiology of Radiocontrast Nephropathy, A Role for Medullary Hypoxia, Invest Radiol, 1999;34:685-691.

Kim et al. Fluoroscopic Landmarks for Optimal Visualization of the Proximal Renal Arteries, JVIR, 10:37-39 (1999).

Stevens, et al., A Prospective Randomized Trial of Prevention Measures in Patients at High Risk for Contrast Nephropathy, J Am Coll Cardiol, 1999;33:403-411.

* cited by examiner

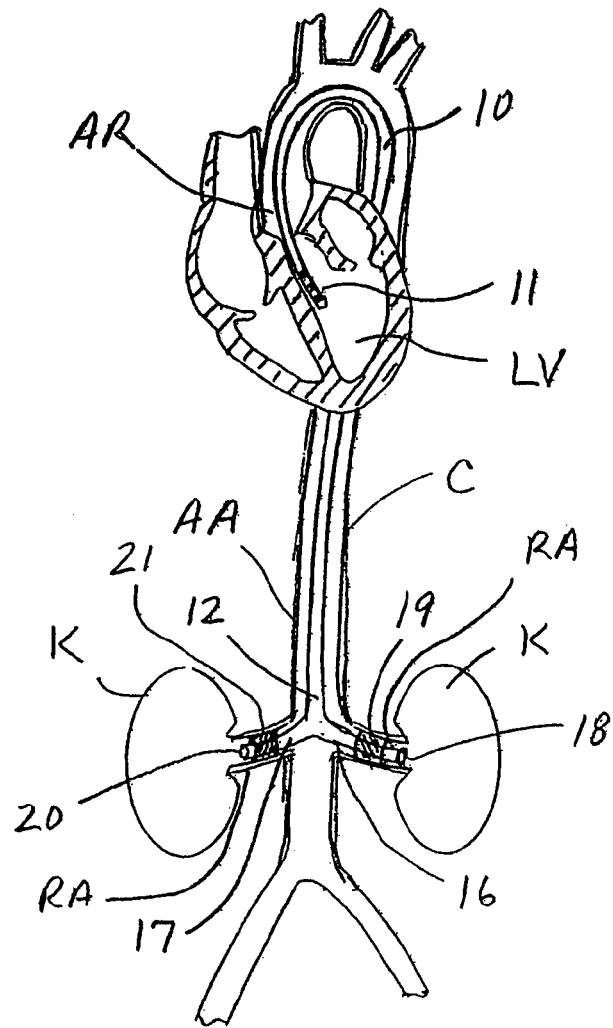
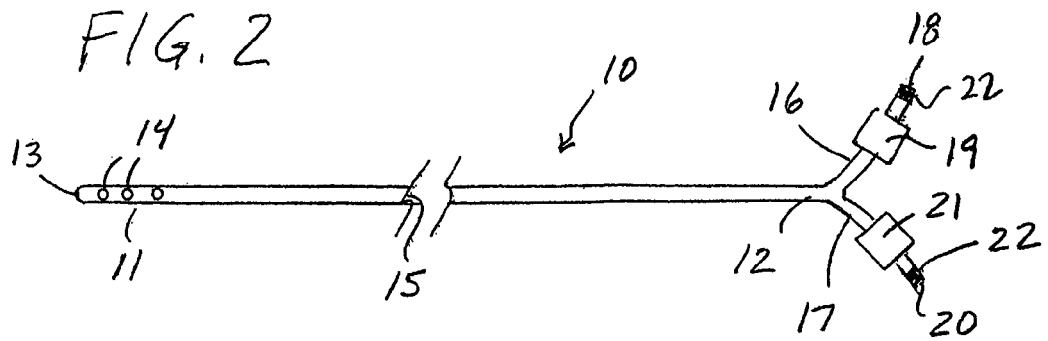
FIG. 1
FIG. 2

APPARATUS AND METHODS FOR TREATING CONGESTIVE HEART DISEASE

CROSS-REFERENCE TO RELATED APPLICATIONS

This application is a continuation of application Ser. No. 09/229,390 filed on Jan. 11, 1999, now U.S. Pat. No. 6,749,598, incorporated herein by reference.

FIELD OF THE INVENTION

The present invention relates to apparatus for treating congestive heart disease by providing increased perfusion to the kidneys, thereby enhancing renal function.

BACKGROUND OF THE INVENTION

It has long been known that cardiac dysfunction induces a series of events that ultimately contribute to congestive heart failure ("CHF"). One such event is a reduction in renal blood flow due to reduced cardiac output. This reduced flow can in turn result in the retention of excess fluid in the patient's body, leading for example, to pulmonary and cardiac edema.

Chapter 62 of *Heart Disease: A Textbook of Cardiovascular Medicine*, (E. Braunwald, ed., 5th ed. 1996), published by Saunders, Philadelphia, Pa., reports that for patients with CHF, the fall in effective renal blood flow is proportional to the reduction in cardiac output. Renal blood flow in normal patients in an age range of 20-80 years averages 600 to 660 ml/min/m$^2$, corresponding to about 14 to 20 percent of simultaneously measured cardiac output. Within a wide spectrum of CHF severity, renal blood flow is depressed to an average range of 250 to 450 ml/min/m$^2$.

Previously known methods of treating congestive heart failure and deteriorating renal function in patients having CHF principally involve administering drugs, including diuretics that enhance renal function, such as furosemide and thiazide, vasopressors intended to enhance renal blood flow, such as Dopamine, and vasodilators that reduce vasoconstriction of the renal vessels. Many of these drugs, when administered in systemic doses, have undesirable side-effects.

In addition, for patients with severe CHF (e.g., those awaiting heart transplant), mechanical methods, such as hemodialysis or left ventricular assist devices, may be implemented. Mechanical treatments, such as hemodialysis, however, generally have not been used for long-term management of CHF.

Advanced heart failure ("HF") requires the combination of potent diuretics and severe restriction of salt intake. Poor patient compliance is a major cause of refractoriness to treatment. On the other hand, as renal urine output decreases with reduced renal perfusion, in the event of dehydration, the required diuretic dosages increase.

In view of the foregoing, it would be desirable to provide methods and apparatus for treating and managing CHF without administering high doses of drugs or dehydrating the patient.

It further would be desirable to provide methods and apparatus for treating and managing CHF by improving blood flow to the kidneys, thereby enhancing renal function.

It also would be desirable to provide methods and apparatus for treating and managing CHF that permit the administration of low doses of drugs, in a localized manner, to improve renal function.

It still further would be desirable to provide methods and apparatus for treating and managing CHF using apparatus that may be percutaneously and transluminally implanted in the patient.

SUMMARY OF THE INVENTION

In view of the foregoing, it is an object of the present invention to provide methods and apparatus for treating and managing CHF without administering high doses of drugs or dehydrating the patient.

It is another object of this invention to provide methods and apparatus for treating and managing CHF by improving blood flow to the kidneys, thereby enhancing renal function.

It is also an object of this invention to provide methods and apparatus for treating and managing CHF that permit the administration of low doses of drugs, in a localized manner, to improve renal function.

It further is an object of the present invention to provide methods and apparatus for treating and managing CHF using apparatus that may be percutaneously and transluminally implanted in the patient.

These and other objects of the present invention are accomplished by providing a catheter having an inlet end configured for placement in a source of arterial blood, such as the aorta, the left ventricle or a femoral artery, and an outlet end having at least one conduit configured to be placed in a renal artery. The catheter includes a lumen through which arterial blood passes directly into a renal artery. The conduit may include means for engaging an interior surface of the renal artery to retain the conduit in position, and may comprise an occluder that reduces backflow of blood exiting the conduit into the abdominal aorta. The catheter preferably is configured to permit percutaneous, transluminal implantation.

In accordance with the principles of the present invention, high pressure blood passes through the lumen of the catheter during systole and into the conduit disposed in the renal artery. It is expected that blood passing through the catheter will have a higher pressure and higher flow rate than blood reaching the renal artery via the abdominal aorta. This in turn is expected to improve renal function, without administering systemic doses of drugs to improve renal function or renal blood flow. The enhanced renal blood flow is expected to provide a proportional increase in renal function, thereby reducing fluid retention.

In alternative embodiments, the catheter may include first and second conduits for perfusing both kidneys, a one-way valve disposed in the lumen to prevent backflow of blood in the lumen during diastole or a mechanical pump to further enhance the flow of blood through the lumen. Still other embodiments of the catheter may include a drug infusion reservoir that injects a low dose of a drug, e.g., a diuretic or vasodilator, into blood flowing through the lumen, so that the drug-infused blood passes directly into the kidneys. Still further embodiments may comprise separate catheters to perfuse the left and right kidneys, or may draw arterial blood from a peripheral vessel using an external pump.

Methods of implanting the apparatus of the present invention also are provided.

BRIEF DESCRIPTION OF THE DRAWINGS

Further features of the invention, its nature and various advantages will be more apparent from the accompanying drawings and the following detailed description of the preferred embodiments, in which:

FIG. 1 is a partial sectional view of a human circulatory system having apparatus constructed in accordance with the present invention implanted therein;

FIG. 2 is a side view of an illustrative embodiment of the apparatus of the present invention;

DETAILED DESCRIPTION OF THE INVENTION

Figure 3:
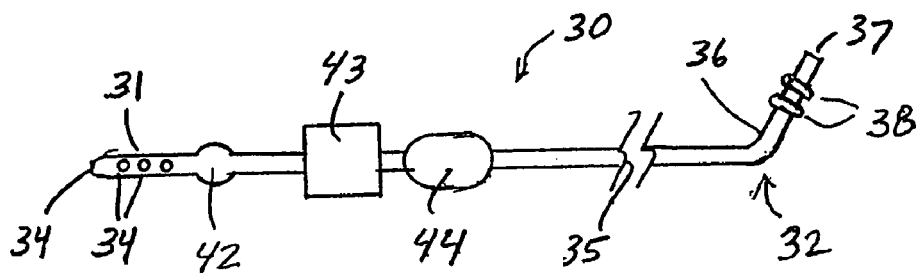
FIG. 3 is an alternative embodiment of the apparatus of FIG. 2 including a one-way valve, a blood pump and a drug infusion device.

The present invention provides a catheter that may be implanted in patients suffering from congestive heart failure ("CHF") to improve renal blood flow and renal function. In accordance with the principles of the present invention, it is expected that by passing blood from the left ventricle directly to the renal arteries during systole, the blood pressure and flow rate in the kidneys will be increased, resulting in enhanced renal function.

Referring to FIGS. 1 and 2, a first illustrative embodiment of apparatus constructed in accordance with the principles of the present invention is described. Catheter 10 comprises hollow flexible tube having inlet end 11 and outlet end 12. Inlet end 11 includes distal hole 13 and lateral holes 14 that communicate with lumen 15 within catheter 10. Outlet end 12 comprises first and second branch conduits 16 and 17, respectively. Catheter 10 preferably comprises a flexible biocompatible material, such as polyurethane, silicone, or polyethylene.

First branch conduit 16 includes outlet port 18 that communicates with lumen 15, and expandable occluder 19. Likewise, second branch conduit 17 includes outlet port 20 that communicates with lumen 15, and expandable occluder 21. First and second branch conduits 16 and 17 optionally may include radio-opaque marker bands 22 near outlet ports 18 and 20, respectively, to assist in implanting catheter 10.

As depicted in FIG. 1, catheter 10 is implanted in circulatory system C so that inlet end 11 is disposed in left ventricle LV or in the vicinity of aortic root AR, while first and second branch conduits 16 and 17, respectively, are disposed in renal arteries RA. Occluders 19 and 21, described in greater detail hereinafter, engage the walls of the renal arteries and retain first and second branch conduits 16 and 17, respectively in position. The occluders also serve to prevent backflow of high pressure blood exiting through outlet ports 18 and 20 from flowing backwards into abdominal aorta AA. Accordingly, blood entering catheter 10 via distal hole 13 and lateral holes 14 during systole passes directly into renal arteries RA and kidneys K through lumen 15, thereby enhancing renal blood flow and renal function.

Referring now to FIG. 3, an alternative embodiment of the apparatus of the present invention is described. Catheter 30 is similar in construction to catheter 10 of FIG. 1, and includes hollow flexible tube having inlet end 31 and outlet end 32. Inlet end 31 includes distal hole 33 and lateral holes 34 that communicate with lumen 35. Outlet end 32 comprises branch conduit 36 having outlet port 37 configured to be placed in one of the patient's renal arteries. In this embodiment, the occluder of the embodiment of FIG. 2 is omitted and instead the diameter of the branch conduit 36 is selected to provide a close fit with the renal artery. Engagement means, such as small ribs or barbs 38 also may be disposed on the exterior surface of branch conduit 36 to retain the branch conduit in the renal artery.

Because the renal arteries may branch from the abdominal aorta at different levels, the catheter of FIG. 3 advantageously permits separate catheters to be used to each perfuse only a single kidney. In addition, the inlet end of catheter 30 may be configured to be placed in a peripheral vessel rather than the left ventricle.

Catheter 30 further optionally comprises any one or more of the following components: one-way valve 42, blood pump 43 or drug infusion device 44. While catheter 30 illustratively includes all three of the foregoing components, it is to be understood that any combination of such components advantageously may be employed.

One-way valve 42, if provided, is configured to open during systole to permit blood to flow through lumen 35 from left ventricle LV towards the renal artery RA, but closes during diastole to prevent the left ventricle from drawing blood in the opposite direction.

Blood pump 43, if provided, may comprise an implantable blood pump, such as are known in the art, and serves to enhance renal blood flow in those patients suffering from severe cardiac dysfunction. Alternatively, where the inlet end of catheter 30 is configured to be placed in a peripheral vessel, blood pump 30 advantageously may comprise an external blood pump, such as are known in the art.

Drug infusion device 44, if provided, preferably comprises an implantable infusion device, such as are known in the art (e.g., for chelation therapy), and periodically infuses low doses of therapeutic agents into blood flowing through lumen 35. Because the infused drugs are delivered directly into the kidneys, smaller doses may be employed, while achieving enhanced therapeutic action and fewer side-effects.

Figure 4:
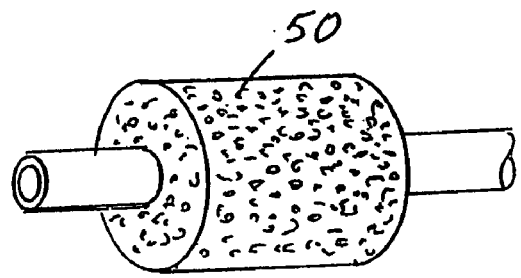
FIG. 4 is a detailed perspective view of an occluder employed on the outlet end of the catheter of FIG. 2.

With respect to FIG. 4, an illustrative embodiment of occluder 50 suitable for use with the catheter of FIGS. 1 and 2 is described. In one embodiment, occluder 50 comprises a low density, biocompatible sponge-like material that may be compressed to a small thickness, and that absorbs and expands when exposed to body fluid. In particular, occluder 50 preferably is compressed to a small thickness and then mounted on the branch conduit so that, when the occluder is deployed in a renal artery, it swells and engages the interior of the renal artery.

Occluder 50 therefore serves to retain the branch conduit in position in a renal artery, and also reduces backflow of blood from the renal artery into the abdominal aorta. Alternatively, occluder 50 may comprise an inflatable member that is inflated and then sealed via a lumen (not shown) extending out of the patient's femoral artery. As a yet further alternative, occluder 50 may comprise a self-expanding hydrogel material that swells when exposed to body fluids to accomplish the functions described hereinabove.

While occluder 50 of FIG. 4 illustratively has an annular shape, it should be understood that other shapes may be employed. For example, occluder 50 may be configured to only partially surround the branch conduit, and may provide only a partial seal with the interior surface of the renal artery. For example, depending upon the relative sizes of the branch conduit and the renal artery, and how far the branch conduit extends into the renal artery, occluder 50 may be omitted altogether.

Figure 5A:
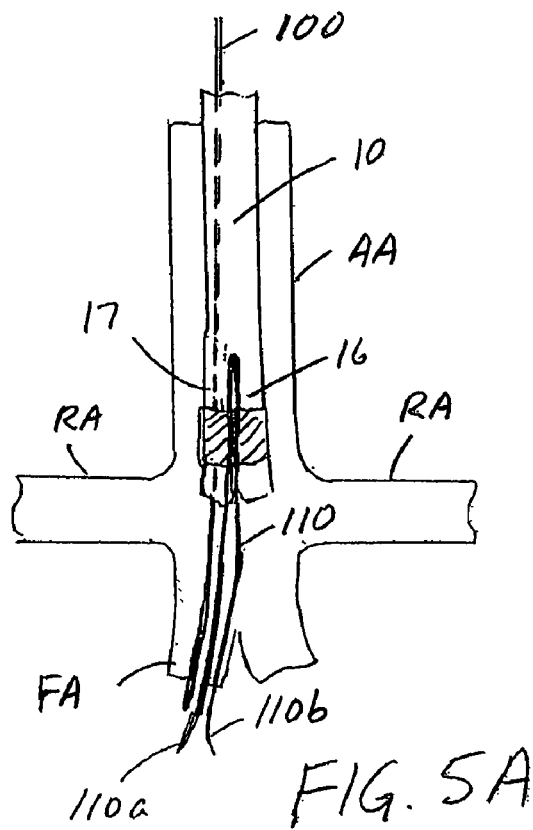
FIGS. 5A and 5B are partial sectional views depicting an illustrative method of implanting the catheter of FIG. 2.
Figure 5B:
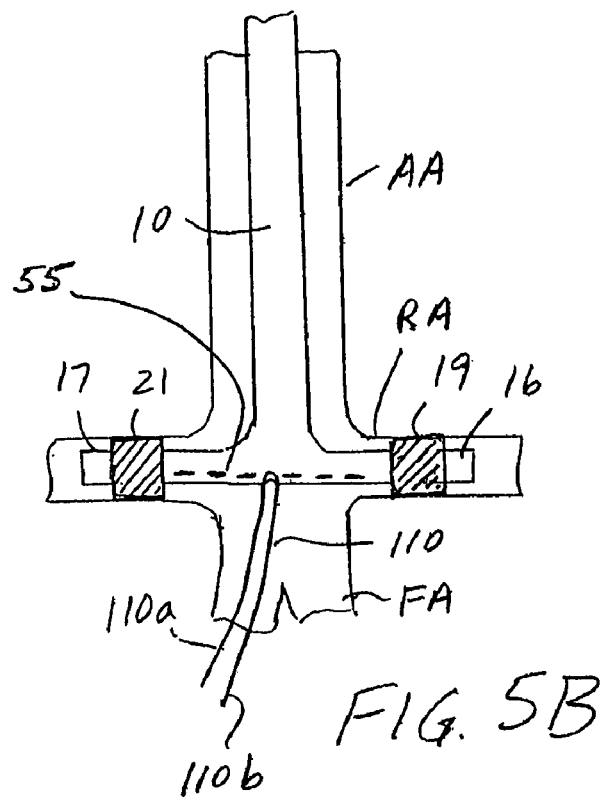

Referring now to FIGS. 1, 5A and 5B, percutaneous, transluminal implantation of the apparatus of FIG. 2 is described. First, guidewire 100 is inserted in a retrograde manner through abdominal aorta AA via an access site in femoral artery FA until the tip of the guidewire is disposed in the left ventricle, e.g., as determined by fluoroscopy. Catheter 10 is then advanced along guidewire 100, for example, using a push tube (not shown) disposed on guidewire 100, with first and second branch conduits 16 and 17 folded side-by-side. Filament 110 is looped through a small opening at the bifurcation of the first and second branch conduits 16 and 17, so that the free ends 110a and 110b of loop 110 may be manipulated by the surgeon.

As depicted in FIG. 5A, catheter 10 is pushed in a distal direction so that outlet ports 18 and 20 of outlet end 12 clear the renal arteries, and guidewire 100 is withdrawn. Filament 110 then is pulled in the proximal direction so that the ends of the first and second branch conduits move into renal arteries RA, as illustrated in FIG. 5B. Strand 55 of an elastic, high strength material, such as a nickel-titanium alloy, may be embedded in the wall of catheter 10 in the bifurcation to ensure that the first and second conduits open outwardly when catheter 10 is pulled in a proximal direction by filament 110.

Once the position of first and second branch conduits 16 and 17 is confirmed, for example, by observing the location of radio-opaque markers 22 (see FIG. 2) with a fluoroscope, occluders 19 and 21 expand to engage the interior surfaces of the renal arteries. Expansion of the occluders may be accomplished either by holding the occluders in place while they expand (if self-expanding) or, if the occluders are inflatable, by injecting a suitable inflation medium.

Filament 110 then may be pulled completely through the opening in the bifurcation of catheter 10, leaving catheter 10 implanted in position. It is expected that the opening needed to accommodate filament 110 will result in negligible loss of blood through the opening once filament 110 has been withdrawn. Alternatively, or in addition, additional guidewires (not shown) may be disposed through first and second branch conduits to assist in placing the first and second branch conduits in renal arteries RA.

The foregoing methods may be readily adapted to implant two catheters of the type illustrated in FIG. 3, so that the branch conduit of each catheter perfuses a separate kidney. In addition, for acute treatment of CHF, the catheter of FIG. 3 (including an external blood pump) may be placed so that the inlet end is disposed in a patient's femoral artery, and the outlet end is disposed in one of the patient's renal arteries.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. An apparatus for locally perfusing one or more kidneys, comprising:
    a catheter having:
        a central lumen;
        an inlet end that includes at least one hole that communicates with the central lumen; and
        an outlet end that includes a first branch conduit with a first outlet port that communicates with the central lumen and a second branch conduit with a second outlet port that communicates with the central lumen;
    a strand of elastic, high strength material;
    a first engagement member coupled with the first branch conduit, the first engagement member adapted to engage an interior surface of a first renal artery; and
    a second engagement member coupled with the second branch conduit, the second engagement member adapted to engage an interior surface of a second renal artery,
    wherein the apparatus can be expanded from a folded configuration where the first branch conduit and the second branch conduit are folded side-by-side, to an expanded configuration where the first branch conduit and the second branch conduit extend outwardly from a bifurcation of the first and second branch conduits, and
    wherein the strand of elastic, high strength material is embedded in the bifurcation of the first and second branch conduits, and is adapted to ensure that the first and second branch conduits open outwardly when the bifurcation is pulled in a proximal direction.

2. The system of claim 1, wherein the fluid agent comprises a diuretic.

3. The system of claim 1, wherein the fluid agent comprises Furosemide.

4. The system of claim 1, wherein the fluid agent comprises Thiazide.

5. The system of claim 1, wherein the fluid agent comprises a vasopressor.

6. The system of claim 1, wherein the fluid agent comprises Dopamine.

7. The system of claim 1, wherein the fluid agent comprises a vasodilator.

8. The apparatus of claim 1, wherein the first engagement member comprises a rib or a barb.

9. The apparatus of claim 1, wherein the first engagement member comprises an inflatable member.

10. The apparatus of claim 1, wherein the first engagement member comprises a self-expanding hydrogel material.

11. The apparatus of claim 1, wherein the first engagement member comprises a low density, biocompatible sponge-like material.

12. The apparatus of claim 1, wherein the strand comprises a nickel-titanium alloy.

13. The apparatus of claim 1, further comprising a one-way valve that communicates with the lumen.

14. The apparatus of claim 1, further comprising a blood pump that communicates with the lumen, wherein the blood pump comprises a member selected from the group consisting of an implantable blood pump and an external blood pump.

15. The apparatus of claim 1, further comprising a drug infusion device that communicates with the lumen.

16. The apparatus of claim 1, further comprising a filament looped through an opening at a bifurcation of the first and second branch conduits.

17. An apparatus for locally perfusing one or more kidneys, comprising:
    a catheter having:
        a central lumen;
        an inlet end that includes at least one hole that communicates with the central lumen; and
        an outlet end that includes a first branch conduit with a first outlet port that communicates with the central lumen and a second branch conduit with a second outlet port that communicates with the central lumen;
    a one-way valve that communicates with the central lumen;
    a first engagement member coupled with the first branch conduit, the first engagement member adapted to engage an interior surface of a first renal artery; and a second engagement member coupled with the second branch conduit, the second engagement member adapted to engage an interior surface of a second renal artery, wherein the apparatus can be expanded from a folded configuration where the first branch conduit and the second branch conduit are folded side-by-side, to an expanded configuration where first branch conduit and the second branch conduit extend outwardly from a bifurcation of the first and second branch conduits, and wherein the one-way valve is adapted to open in a first configuration to permit flow along the central lumen in a first direction from the inlet end toward the first outlet port, the second outlet port, or both, and to close in a second configuration to inhibit flow along the central lumen in a second direction from the first outlet port, the second outlet port, or both, toward the inlet end.

18. The apparatus of claim 17, further comprising a strand of an elastic, high strength material embedded in the bifurcation.

19. The apparatus of claim 18, wherein the strand comprises a nickel-titanium alloy.

20. The system of claim 17, wherein the fluid agent comprises a diuretic.

21. The system of claim 17, wherein the fluid agent comprises Furosemide.

22. The system of claim 17, wherein the fluid agent comprises Thiazide.

23. The system of claim 17, wherein the fluid agent comprises a vasopressor.

24. The system of claim 17, wherein the fluid agent comprises Dopamine.

25. The system of claim 17, wherein the fluid agent comprises a vasodilator.

26. The apparatus of claim 17, wherein the first engagement member comprises a rib or a barb.

27. The apparatus of claim 17, wherein the first engagement member comprises an inflatable member.

28. The apparatus of claim 17, wherein the first engagement member comprises a self-expanding hydrogel material.

29. The apparatus of claim 17, wherein the first engagement member comprises a low density, biocompatible sponge-like material.

30. The apparatus of claim 17, further comprising a blood pump that communicates with the lumen, wherein the blood pump comprises a member selected from the group consisting of an implantable blood pump and an external blood pump.

31. The apparatus of claim 17, further comprising a drug infusion device that communicates with the lumen.

32. The apparatus of claim 17, further comprising a filament looped through an opening at a bifurcation of the first and second branch conduits.

* * * * *